(12) United States Patent
Keim et al.

(10) Patent No.: US 8,808,993 B2
(45) Date of Patent: Aug. 19, 2014

(54) METHODS AND KITS TO DETECT NEW H1N1 "SWINE FLU" VARIANTS

(75) Inventors: Paul Keim, Flagstaff, AZ (US); Elizabeth Driebe, Flagstaff, AZ (US); David Engelthaler, Flagstaff, AZ (US)

(73) Assignees: The Translational Genomics Research Institute, Phoenix, AZ (US); Arizona Board of Regents on Behalf of Northern Arizona University, Flagstaff, AZ (US)

( * ) Notice: Subject to any disclaimer, the term of this patent is extended or adjusted under 35 U.S.C. 154(b) by 223 days.

(21) Appl. No.: 12/917,357

(22) Filed: Nov. 1, 2010

(65) Prior Publication Data

US 2012/0107796 A1    May 3, 2012

(51) Int. Cl.
*C12Q 1/68*    (2006.01)
(52) U.S. Cl.
USPC ........................................ 435/6.12
(58) Field of Classification Search
None
See application file for complete search history.

(56) References Cited

U.S. PATENT DOCUMENTS 8,097,419 B2 * 1/2012 Fischer et al. ............... 435/6.12
2009/0098527 A1 * 4/2009 Fischer et al. ................... 435/5

OTHER PUBLICATIONS

NCBI Accession No. FJ986328 (May 6, 2009).*
NCBI Accession No. DQ107491 (Oct. 7, 2005).*
NCBI Accession No. AY575904 (Jun. 4, 2004).*
NCBI Accession No. DQ186975 (Sep. 1, 2006).*
NCBI Accession No. CY047718 (Oct. 15, 2009).*
NCBI Accession No. DQ250165 (Feb. 21, 2006).*
Buck et al. (Biotechniques. 1999. 27(3): pp. 528-536).*
Lowe et al. (Nucleic Acids Research, vol. 18, No. 7, p. 1757-1761, 1990).*
Okimoto et al., Improved PCR Amplification of Multiple Specific Alleles•(PAMSA) Using Internally Mismatched Primers, BioTechniques 21:20-26 (Jul. 1996).*
Bloom et al. (Permissive Secondary Mutations Enable the Evolution of Influenza Oseltamivir Resistance, Science, vol. 328, pp. 1272-1275, Jun. 2010).*
Maritz et al. (Pandemic influenza A (H1N1) 2009: the experience of the first six months, Clin Chem Lab Med 2010;48(1):11-21, published online Dec. 22, 2009).*

* cited by examiner

*Primary Examiner* — Christopher M Babic
*Assistant Examiner* — Aaron Priest

(57) ABSTRACT

Methods and kits used in the detection of the H1N1/09 influenza virus are provided. The methods include the use of nucleic acids to detect H1N1/09 generally as well as H1N1/09 variants resistant to antiviral compositions.

19 Claims, 3 Drawing Sheets

SEQUENCE LISTING

```
<160> NUMBER OF SEQ ID NOS: 15

<210> SEQ ID NO 1
<211> LENGTH: 30
<212> TYPE: DNA
<213> ORGANISM: Influenza A virus

<400> SEQUENCE: 1
acaacatgga tagagcagtt aaactataca                                    30

<210> SEQ ID NO 2
<211> LENGTH: 27
<212> TYPE: DNA
<213> ORGANISM: Influenza A virus

<400> SEQUENCE: 2
accagttgaa tagcttagtg acacctc                                       27

<210> SEQ ID NO 3
<211> LENGTH: 18
<212> TYPE: DNA
<213> ORGANISM: Influenza A virus

<400> SEQUENCE: 3
ctcaaaagag aaataacg                                                 18

<210> SEQ ID NO 4
<211> LENGTH: 23
<212> TYPE: DNA
<213> ORGANISM: Influenza A virus

<400> SEQUENCE: 4
gaaaatttgc aggcctacca gaa                                           23

<210> SEQ ID NO 5
<211> LENGTH: 22
<212> TYPE: DNA
<213> ORGANISM: Influenza A virus

<400> SEQUENCE: 5
aggtgcaaga tcccaatgat gc                                            22

<210> SEQ ID NO 6
<211> LENGTH: 22
<212> TYPE: DNA
<213> ORGANISM: Influenza A virus

<400> SEQUENCE: 6
aggtgcaaga tcccaatgat gt                                            22

<210> SEQ ID NO 7
<211> LENGTH: 17
<212> TYPE: DNA
<213> ORGANISM: Influenza A virus
```

<400> SEQUENCE: 7
tgcagcgatt caagtga                                              17

<210> SEQ ID NO 8
<211> LENGTH: 24
<212> TYPE: DNA
<213> ORGANISM: Influenza A virus

<400> SEQUENCE: 8
tratgaccga tggaccaagt aatg                                      24

<210> SEQ ID NO 9
<211> LENGTH: 26
<212> TYPE: DNA
<213> ORGANISM: Influenza A virus

<400> SEQUENCE: 9
ggataacagg agcattcctc atattg                                    26

<210> SEQ ID NO 10
<211> LENGTH: 26
<212> TYPE: DNA
<213> ORGANISM: Influenza A virus

<400> SEQUENCE: 10
ggataacagg agcattcctc atatta                                    26

<210> SEQ ID NO 11
<211> LENGTH: 17
<212> TYPE: DNA
<213> ORGANISM: Influenza A virus

<400> SEQUENCE: 11
acaggcctca tacaaga                                              17

<210> SEQ ID NO 12
<211> LENGTH: 97
<212> TYPE: PRT
<213> ORGANISM: Influenza A virus

<400> SEQUENCE: 12

Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Val Ala Ala Ser Ile
            20                  25                  30

Ile Gly Ile Val His Leu Ile Leu Trp Ile Ile Asp Arg Leu Phe Ser
        35                  40                  45

Lys Ser Ile Tyr Arg Ile Phe Lys His Gly Leu Lys Arg Gly Pro Ser
    50                  55                  60

Thr Glu Gly Val Pro Glu Ser Met Arg Glu Glu Tyr Arg Glu Glu Gln
65                  70                  75                  80

Gln Asn Ala Val Asp Ala Asp Asp Gly His Phe Val Ser Ile Glu Leu
                85                  90                  95

Glu

<210> SEQ ID NO 13
<211> LENGTH: 294
<212> TYPE: DNA
<213> ORGANISM: Influenza A virus

<400> SEQUENCE: 13

```
atgagtcttc taaccgaggt cgaaacgcct atcagaaacg aatggggtg cagatgcaac      60 gattcaagtg atcctcttgt tgttgccgca agtataattg ggattgtgca cctgatattg    120
tggattattg atcgcctttt ttccaaaagc atttatcgta tctttaaaca cggttttaaaa   180 agagggcctt ctacgaagg agtaccagag tctatgaggg aagaatatcg agaggaacag     240
cagaatgctg tggatgctga cgatggtcat tttgtcagca tagagctgga gtaa          294
```

```
<210> SEQ ID NO 14
<211> LENGTH: 469
<212> TYPE: PRT
<213> ORGANISM: Influenza A virus

<400> SEQUENCE: 14

Met Asn Pro Asn Gln Lys Ile Ile Thr Ile Gly Ser Ile Ser Ile Ala
1               5                   10                  15

Ile Gly Ile Ile Ser Leu Met Leu Gln Ile Gly Asn Ile Ile Ser Ile
            20                  25                  30

Trp Ala Ser His Ser Ile Gln Thr Gly Ser Gln Asn His Thr Gly Val
        35                  40                  45

Cys Asn Gln Arg Ile Ile Thr Tyr Glu Asn Ser Thr Trp Val Asn His
    50                  55                  60

Thr Tyr Val Asn Ile Asn Asn Thr Asn Val Val Ala Gly Lys Asp Lys
65                  70                  75                  80

Thr Ser Val Thr Leu Ala Gly Asn Ser Ser Leu Cys Ser Ile Ser Gly
                85                  90                  95

Trp Ala Ile Tyr Thr Lys Asp Asn Ser Ile Arg Ile Gly Ser Lys Gly
            100                 105                 110

Asp Val Phe Val Ile Arg Glu Pro Phe Ile Ser Cys Ser His Leu Glu
        115                 120                 125

Cys Arg Thr Phe Phe Leu Thr Gln Gly Ala Leu Leu Asn Asp Lys His
    130                 135                 140

Ser Asn Gly Thr Val Lys Asp Arg Ser Pro Tyr Arg Ala Leu Met Ser
145                 150                 155                 160

Cys Pro Leu Gly Glu Ala Pro Ser Pro Tyr Asn Ser Lys Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Glu Thr Ile Lys Ser Trp Lys Lys Arg Ile Leu
    210                 215                 220

Arg Thr Gln Glu Ser Glu Cys Val Cys Val Asn Gly Ser Cys Phe Thr
225                 230                 235                 240

Ile Met Thr Asp Gly Pro Ser Asn Gly Ala Ala Ser Tyr Lys Ile Phe
                245                 250                 255

Lys Ile Glu Lys Gly Lys Val Thr Lys Ser Ile Glu Leu Asn Ala Pro
            260                 265                 270

Asn Phe His Tyr Glu Glu Cys Ser Cys Tyr Pro Asp Thr Gly Thr Val
        275                 280                 285

Met Cys Val Cys Arg Asp Asn Trp His Gly Ser Asn Arg Pro Trp Val
    290                 295                 300

Ser Phe Asn Gln Asn Leu Asp Tyr Gln Ile Gly Tyr Ile Cys Ser Gly
305                 310                 315                 320
```

```
Val Phe Gly Asp Asn Pro Arg Pro Lys Asp Gly Glu Gly Ser Cys Asn
                325                 330                 335

Pro Val Thr Val Asp Gly Ala Asp Gly Val Lys Gly Phe Ser Tyr Lys
            340                 345                 350

Tyr Gly Asn Gly Val Trp Ile Gly Arg Thr Lys Ser Asn Arg Leu Arg
        355                 360                 365

Lys Gly Phe Glu Met Ile Trp Asp Pro Asn Gly Trp Thr Asp Thr Asp
    370                 375                 380

Ser Asp Phe Ser Val Lys Gln Asp Val Val Ala Ile Thr Asp Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Val Arg Gly Leu Pro Arg
                420                 425                 430

Glu Asn Thr Thr Ile Trp Thr Ser Gly Ser Ser Ile Ser Phe Cys Gly
                435                 440                 445

Val Asn Ser Asp Thr Ala Asn Trp Ser Trp Pro Asp Gly Ala Glu Leu
            450                 455                 460

Pro Phe Thr Ile Asp
465

<210> SEQ ID NO 15
<211> LENGTH: 1457
<212> TYPE: DNA
<213> ORGANISM: Influenza A virus

<400> SEQUENCE: 15
agcaaaagca ggagtttaaa atgaacccaa atcaaaagat aataaccatt ggatcaatca      60
gtatagcaat cggaataatt agtctaatgt tgcaaatagg aaatattatt tcaatatggg     120
ctagtcactc aatccaaact ggaagtcaaa acaacactgg aatatgcaac caaagaatca     180
tcacatatga aaacagcacc tgggtgaatc acacatatgt taatattaac aacactaaag     240
ttgttgctgg agaggacaaa acttcagtga cattggccgg caattcatct ctttgttcta     300
tcagtggatg gctatatac acaaaagaca acagcataag aattggctcc aaaggagatg     360
tttttgtcat aagagaacct ttcatatcat gttctcactt ggaatgcaga accttttttc     420
tgacccaagg cgctctatta aatgacaaac attcaaatgg accgtaaag acagaagtc      480 cttatagggc ttaatgagc tgtcctctag gtgaagctcc gtccccatac aattcaaagt     540
tcgaatcagt tgcatggtca gcaagcgcat gccatgatgg catgggctgg ttaacaatcg     600
gaatttctgg tccagacaat ggagctgtgg ctgtactaaa atacaacgga ataataactg     660
gaaccataaa aagttggaaa agcaaatat taagaacaca agagtctgaa tgtgtctgta     720
tgaacgggtc atgtttcacc ataatgaccg atggcccgag taataaggcc gcctcttaca     780 aaatttttcaa gatcgaaaag gggaaggtta ctaaatcaat agagttgaat gcacccaatt     840
tttattatga ggaatgctcc tgttacccag acactggcat agtgatgtgt gtatgcaggg     900
acaactggca tggttcaaat cgaccttggg tgtcttttaa tcaaaacttg gattatcaaa     960
taggatacat ctgcagtgga gtgtttggtg acaatccgcg tcccgaagat ggagagggca    1020
gctgcaatcc agtgactgtt gatggagcaa acggagtaaa agggttttca tacaaatatg    1080 gtaatgggt ttggatagga aggaccaaaa gtaacagact agaaaggggg tttgagatga    1140
tttgggatcc taatggatgg acaaatacccg acagtgattt ctcagtgaaa caggatgttg    1200
tagcaataac tgattggtca gggtacagcg gaagtttcgt ccaacatcct gagttaacag    1260
```

-continued

```
gattggactg tataagacct tgcttctggg ttgagttagt cagagggctg cctagagaaa   1320
atacaacaat ctggactagt gggagcagca tttctttttg tggcgttaat agtgatactg   1380
caaactggtc ttggccagac ggtgctgagt tgccgttcac catcgacaag tagttcgttg   1440
aaaaaactcc ttgtttc                                                  1457
```

US 8,808,993 B2

METHODS AND KITS TO DETECT NEW H1N1 "SWINE FLU" VARIANTS

BACKGROUND OF THE INVENTION

Surveillance and therapy of the H1N1/09 influenza variant, (which may also be known as as "novel H1N1," "swine flu," and "Mexican flu," among others) requires monitoring of patients with influenza symptoms as well as tracking of subpopulations and strains. Assays that track such subpopulations should rapidly, quantitatively, sensitively and specifically detect the subpopulations in mixed concentrations of antiviral sensitive viruses.

BRIEF SUMMARY OF THE INVENTION

The present invention provides among other things: compositions and methods used to detect Influenza virus variants.

It is an object of the invention to detect H1N1/09 in patients.

It is an object of the invention to detect mutant forms of H1N1/09 that confer resistance to antiviral drugs.

It is an object of the invention to provide an assay to detect antiviral resistant forms of H1N1/09 that is easily translatable for clinical and public health diagnostic use.

It is an object of the invention to determine whether or not H1N1/09 is present in a sample.

It is an object of the invention to determine whether or not an H1N1/09 strain resistant to an antiviral composition is present in a sample.

It is an object of the invention to provide a kit used in the detection of Influenza variants.

The above and other objects may be achieved through the use of methods involving adding a first oligonucleotide that includes a sequence selected from the group consisting of SEQ ID NO. 1, SEQ ID NO. 2, and SEQ ID NO. 3 to a first mixture comprising the sample, subjecting the mixture to conditions that allow nucleic acid amplification, and classifying the subject into a cohort on the basis of a result of the nucleic acid amplification, wherein the cohort is selected from a group consisting of a cohort of samples in which H1N1/09 is present and a cohort of samples in which H1N1/09 is absent. If the first oligonucleotide includes SEQ ID NO. 1, then the method may further comprise adding a second oligonucleotide to the first mixture. The second oligonucleotide may be any oligonucleotide such as an oligonucleotide that includes SEQ ID NO. 2. The method may further comprise adding a third oligonucleotide to the first mixture. The third oligonucleotide may be any oligonucleotide such as an oligonucleotide that includes SEQ ID NO. 3. The third oligonucleotide may comprise a label. The label may be any label such as a fluorescent label. Examples of fluorescent labels include: FAM, dR110, 5-FAM, 6FAM, dR6G, JOE, HEX, VIC, TET, dTAMRA, TAMRA, NED, dROX, PET, BHQ+, Gold540, and LIZ. The result may be any result of a nucleic acid amplification such as a Ct value or a nucleic acid sequence. The sample may be any sample such as an environmental sample or a sample from a subject. Examples of samples derived from a subject include: a sputum sample and a respiratory swab.

The above and other objects may be achieved through the use of methods involving adding a first oligonucleotide to first mixture comprising the sample, wherein the first oligonucleotide includes a sequence selected from the group consisting of SEQ ID NO. 1, SEQ ID NO. 2, and SEQ ID NO. 3, adding a second oligonucleotide to second mixture comprising the sample, wherein the second oligonucleotide includes a sequence selected from the group consisting of SEQ ID NO. 4, SEQ ID NO. 5, SEQ ID NO. 6, SEQ ID NO. 7, SEQ ID NO. 8, SEQ ID NO. 9, SEQ ID NO. 10, and SEQ ID NO. 11. Both the first and second mixtures are subjected to conditions that allow nucleic acid amplification. The samples are classified into a cohort on the basis of the nucleic acid amplifications of the first mixture and the second mixture. The cohort is selected from the group consisting of: a cohort of samples in which H1N1/09 is absent, a cohort of samples in which a strain of H1N1/09 that is sensitive to an antiviral composition is present, and a cohort of samples in which a strain of H1N1/09 that is resistant to an antiviral composition is present. If the second oligonucleotide includes SEQ ID NO. 4, then the method may further comprise adding a third oligonucleotide to the second mixture. The third oligonucleotide may be any oligonucleotide including an oligonucleotide with a sequence selected from the group consisting of SEQ ID NO. 5 and SEQ ID NO. 6. The method may further comprise adding a fourth nucleotide to the second mixture wherein the fourth oligonucleotide includes SEQ ID NO. 7. Alternatively the method may comprise adding a second oligonucleotide to the second mixture wherein the second oligonucleotide includes SEQ ID NO. 8 and the alternative method may further comprise adding a third oligonucleotide to the second mixture. The third oligonucleotide may be any oligonucleotide such as an oligonucleotide that includes a sequence selected from the group consisting of SEQ ID NO. 9 and SEQ ID NO. 10. The method may further comprise adding a fourth oligonucleotide to the second mixture, wherein the fourth oligonucleotide includes SEQ ID NO. 11. If the second oligonucleotide includes a sequence selected from the group consisting of SEQ ID NO. 4, SEQ ID NO. 5, SEQ ID NO. 6, and SEQ ID NO. 7, then the antiviral composition may comprise an adamantane. If the second nucleic acid includes a sequence selected from the group consisting of SEQ ID NO. 8, SEQ ID NO. 9, SEQ ID NO. 10, and SEQ ID NO. 11, then the antiviral composition may comprise a neuraminidase inhibitor.

The above and other objects may be achieved through the use of kits involving a first oligonucleotide that includes a sequence selected from the group consisting of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, and SEQ ID NO. 11 and an indication of a result that signifies the presence of an H1N1/09 strain of a type selected from the group consisting of H1N1/09 resistant to an antiviral composition, and H1N1/09 sensitive to an antiviral composition. The kit may further comprise an indication of a result that signifies the absence of an H1N1/09 strain. The kit may further comprise an enzyme. The enzyme may be any enzyme such as a reverse transcriptase or a DNA polymerase, such as a thermostable DNA polymerase. The result may comprise a $\Delta Ct$ value, a $\Delta Ct_{r-s}$ value, or a nucleic acid sequence. The indication may be any indication such as a positive control or a writing such as an amplification plot. A writing may be physically contained within the kit or made available via a website.

BRIEF DESCRIPTION OF THE FIGURES

A more complete understanding of the present invention may be derived by referring to the detailed description when considered in connection with the following illustrative figures.

Figure 1:
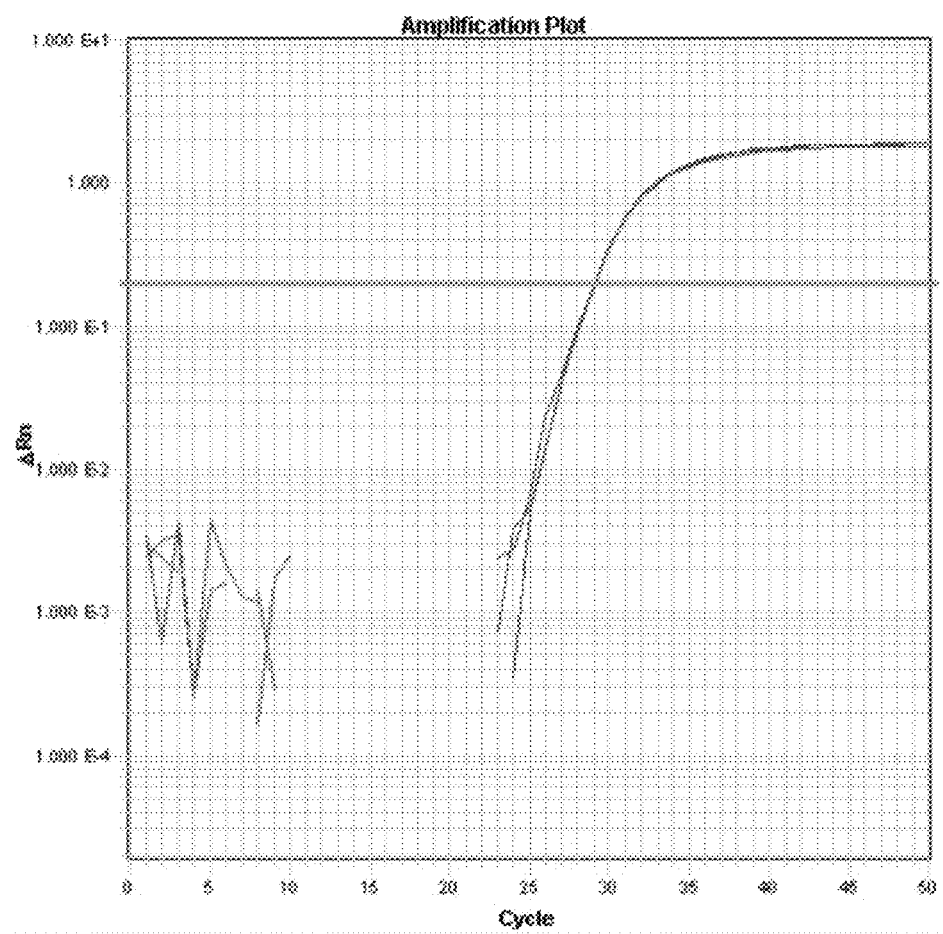
FIG. 1 depicts an amplification plot of an H1N1/09 sample using a primer/probe set that includes SEQ ID NO. 1, SEQ ID NO. 2, and SEQ ID NO. 3.

Elements and acts in the figures are illustrated for simplicity and have not necessarily been rendered according to any particular sequence or embodiment.

DETAILED DESCRIPTION OF THE INVENTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention.

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts. Inventors are fully aware that they can be their own lexicographers if desired.

Inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that the noun, term, or phrase is given its broadest possible meaning Further, the inventors are fully informed of the standards and application of the special provisions of 35 U.S.C. §112, ¶6. Thus, the use of the words "function," "means" or "step" in the Detailed Description or Description of the Drawings or claims is not intended to somehow indicate a desire to invoke the special provisions of 35 U.S.C. §112, ¶6, to define the invention. To the contrary, if the provisions of 35 U.S.C. §112, ¶6 are sought to be invoked to define the inventions, the claims will specifically and expressly state the exact phrases "means for" or "step for, and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventors not to invoke the provisions of 35 U.S.C. §112, ¶6. Moreover, even if the provisions of 35 U.S.C. §112, ¶6 are invoked to define the claimed inventions, it is intended that the inventions not be limited only to the specific structure, material or acts that are described in the preferred embodiments, but in addition, include any and all structures, materials or acts that perform the claimed function as described in alternative embodiments or forms of the invention, or that are well known present or later-developed, equivalent structures, material or acts for performing the claimed function Investigators herein disclose compositions of matter and methods used to detect and/or quantify H1N1/09 influenza virus and variants thereof including variants that confer resistance to antiviral compositions.

A marker may be any molecular structure produced by a cell, expressed inside the cell, accessible on the cell surface, or secreted by the cell. A marker may be any protein, carbohydrate, fat, nucleic acid, catalytic site, or any combination of these such as an enzyme, glycoprotein, cell membrane, virus, cell, organ, organelle, or any uni- or multimolecular structure or any other such structure now known or yet to be disclosed whether alone or in combination. A marker may also be called a target and the terms are used interchangeably.

A marker may be represented by the sequence of a nucleic acid from which it can be derived. Examples of such nucleic acids include miRNA, tRNA, siRNA, mRNA, cDNA, or genomic DNA sequences. While a marker may be represented by the sequence of a single nucleic acid strand (e.g. 5'→3'), nucleic acid reagents that bind the marker may also bind to the complementary strand (e.g. 3'→5'). Alternatively, a marker may be represented by a protein sequence. The concept of a marker is not limited to the products of the exact nucleic acid sequence or protein sequence by which it may be represented. Rather, a marker encompasses all molecules that may be detected by a method of assessing the expression of the marker.

When a nucleic acid includes a particular sequence, the sequence may be a part of a longer nucleic acid or may be the entirety of the sequence. The nucleic acid may contain nucleotides 5' of the sequence, 3' of the sequence, or both. The concept of a nucleic acid including a particular sequence further encompasses nucleic acids that contain less than the full sequence that are still capable of specifically detecting a marker. Nucleic acid sequences may be identified by the IUAPC letter code which is as follows: A—Adenine base; C—Cytosine base; G—guanine base; T or U—thymine or uracil base. M-A or C; R-A or G; W-A or T; S-C or G; Y-C or T; K-G or T; V-A or C or G; H-A or C or T; D-A or G or T; B-C or G or T; N or X-A or C or G or T. Note that T or U may be used interchangeably depending on whether the nucleic acid is DNA or RNA. A reagent capable of binding to a nucleic acid sequence having less than 60% 70%, 80%, 90%, 95%, 99% or 100% identity to the identifying sequence may still be encompassed by the invention if it is still capable of binding to its complimentary sequence and/or facilitating nucleic acid amplification of a desired sequence. Although a nucleic acid sequence represented by the sequence of a single nucleic acid strand (e.g. the 5'→3' strand) the totality of reagents that bind to the sequence also includes all reagents capable of binding to the complementary strand (e.g the 3'→5' strand). If a sequence is represented in degenerate form; for example through the use of codes other than A, C, G, T, or U; the concept of a nucleic acid including the sequence also encompasses a mixture of nucleic acids of different sequences that still meet the conditions imposed by the degenerate sequence. Examples of molecules encompassed by a marker represented by a particular sequence or structure include point mutations, silent mutations, deletions, frameshift mutations, translocations, alternative splicing derivatives, differentially methylated sequences, truncations, soluble forms of cell membrane associated markers, and any other variation that results in a product that may be identified as the marker. The following nonlimiting examples are included for the purposes of clarifying this concept: If expression of a specific marker in a sample is assessed by PCR, and if the sample expresses an DNA sequence different from the sequence used to identify the specific marker by one or more nucleotides, but the marker may still be detected using PCR, then the specific marker encompasses the sequence present in the sample. A marker may also be represented by a protein sequence, which includes mutated and differentially modified protein sequences.

The invention may comprise methods detecting the presence of a particular virus in a sample. A sample may be derived from anywhere that a virus or any part of a virus may be found including soil, air, water, solid surfaces (whether natural or artificial,) culture media, foodstuffs, and any interfaces between or combinations of these elements. Additionally, a sample may be derived from a subject, such as a plant or animal, including humans. Samples derived from animals include but are not limited to biopsy or other in vivo or ex vivo analysis of prostate, breast, skin, muscle, facia, brain, endometrium, lung, head and neck, pancreas, small intestine, blood, liver, testes, ovaries, colon, skin, stomach, esophagus, spleen, lymph node, bone marrow, kidney, placenta, or fetus. Samples derived from subjects may also take the form of a fluid sample such as peripheral blood, lymph fluid, ascites, serous fluid, pleural effusion, sputum, bronchial wash, bronchioalveolar lavage fluid (BALF,) cerebrospinal fluid, semen, amniotic fluid, lacrimal fluid, stool, urine, hair, or any other source in which a fungus, or any part of a fungus might be present. Samples collected from a plant may be collected from part of a plant or from an entire plant. Samples may be collected by any method now known or yet to be disclosed, including swiping or swabbing an area or orifice, removal of a piece of tissue as in a biopsy, or any method known to collect bodily fluids. Samples may be suspected of containing a virus if they are derived from a subject displaying symptoms of a viral infection or from an environmental sample from an area in which a virus is thought to be present.

Direct methods of detecting the presence of a marker include but are not limited to any form of DNA sequencing including Sanger, next generation sequencing, pyrosequencing, SOLID sequencing, massively parallel sequencing, pooled, and barcoded DNA sequencing or any other sequencing method now known or yet to be disclosed; PCR-based methods such as real-time PCR, quantitative PCR, or any combination of these; allele specific ligation; comparative genomic hybridization; array based genotyping including SNP genotyping, or any other method that allows the detection of a particular nucleic acid sequence within a sample or enables the differentiation of one nucleic acid from another nucleic acid that differs from the first nucleic acid by one or more nucleotides. A sample may be suspected of including a nucleic acid from a fungus of interest. A subject may be any organism that may be infected by a virus including bacteria, plants, animals, chordates, mammals, humans, insects, endangered species, or any other organism of agricultural, environmental, or other significance.

In Sanger Sequencing, a single-stranded DNA template, a primer, a DNA polymerase, nucleotides and a label such as a radioactive label conjugated with the nucleotide base or a fluorescent label conjugated to the primer, and one chain terminator base comprising a dideoxynucleotide (ddATP, ddGTP, ddCTP, or ddTTP, are added to each of four reaction (one reaction for each of the chain terminator bases). The sequence may be determined by electrophoresis of the resulting strands. In dye terminator sequencing, each of the chain termination bases is labeled with a fluorescent label of a different wavelength which allows the sequencing to be performed in a single reaction.

In pyrosequencing, the addition of a base to a single stranded template to be sequenced by a polymerase results in the release of a phyrophosphate upon nucleotide incorporation. An ATP sulfyrlase enayme converts pyrophosphate into ATP which in turn catalyzes the conversion of luciferin to oxyluciferin which results in the generation of visible light that is then detected by a camera.

In SOLiD sequencing, the molecule to be sequenced is fragmented and used to prepare a population of clonal magnetic beads (in which each bead is conjugated to a plurality of copies of a single fragment) with an adaptor sequence and alternatively a barcode sequence The beads are bound to a glass surface. Sequencing is then performed through 2-base encoding.

In massively parallel sequencing, randomly fragmented DNA is attached to a surface. The fragments are extended and bridge amplified to create a flow cell with clusters, each with a plurality of copies of a single fragment sequence. The templates are sequenced by synthesizing the fragments in parallel. Bases are indicated by the release of a fluorescent dye correlating to the addition of the particular base to the fragment.

Indirect methods of detecting a marker generally involve assessing the expression of material created from a genomic DNA template such as a RNA or protein molecule. Such expression may be assessed by any of a number of methods used currently in the art and yet to be developed. Examples include any nucleic acid detection method including the following nonlimiting examples, microarray RNA analysis, RNA in situ hybridization, RNAse protection assay, Northern blot, reverse transcription PCR, and quantitative reverse transcription PCR. Other examples include any process of detecting expression that uses an antibody including the following nonlimiting examples, flow cytometry, immunohistochemistry, ELISA, Western blot, Northwestern blot, and immunoaffinity chromatograpy. Antibodies may be monoclonal, polyclonal, or any antibody fragment including an Fab, $F(ab)_2$, Fv, scFv, phage display antibody, peptibody, multispecific ligand, or any other reagent with specific binding to a target. Other methods of assessing protein expression include the following nonlimiting examples: HPLC, mass spectrometry, protein microarray analysis, PAGE analysis, isoelectric focusing, 2-D gel electrophoresis, and enzymatic assays.

A reagent may be any substance that facilitates any method of detecting a marker. Examples of reagents include nucleic acids such as oligonucleotide probes, nucleic acid mixtures, or full length nucleic acids; proteins such as antibodies, natural ligands, or enzymes; or small molecule compounds in or out of solution such as drugs, buffers, vitamins, or any other artificial or naturally occurring compound that may facilitate the detection of a marker. A reagent may be capable of specific binding to the marker such as a nucleic acid probe or antibody with specificity for the marker.

A reagent may be added to a sample by any of a number of methods including manual methods, mechanical methods, or any combination thereof. The presence of the marker may be signified by any of a number of methods including amplification of a specific nucleic acid sequence, sequencing of a native or amplified nucleic acid, or the detection of a label either bound to or released as a result of the detection of the marker. Addition of a reagent capable of specifically binding a marker to a sample also encompasses addition of the reagent to a sample in which the marker to which the nucleic acid has specificity is absent.

In some aspects of the invention, the presence of a marker may be established by binding to a microarray such as a DNA chip. Examples of DNA chips include chips in which a number of single stranded oligonucleotide probes are affixed to a solid substrate such as silicon glass. Oligonucleotides capable of binding to a marker are capable of hybridizing to all or part of the marker to the exclusion of sequences that differ from those included within the marker by one or more nucleotides. The number of nucleotide differences that may be tolerated are dependant upon the hybridization conditions. Labeled sample DNA is hybridized to the oligonucleotides and detection of the label is correlated with binding of the sample and consequently the presence of the allele in the sample.

In allele-specific hybridization, oligonucleotide sequences representing all possible variations at a polymorphic site are included on a chip. The chip and sample are subject to conditions under which the labeled sample DNA will bind only to an oligonucleotide with an exact sequence match. In allele-specific primer extension, sample DNA hybridized to the chip may be used as a synthesis template with the affixed oligonucleotide as a primer. Under this method, only the added dNTP's are labeled. Incorporation of the labeled dNTP then serves as the signal indicating the presence of the allele. The fluorescent label may be detected by any of a number of instruments configured to read at least four different fluorescent labels on a DNA chip. In another alternative, the identity of the final dNTP added to the oligonucleotide may be assessed by mass spectrometry. In this alternative, the dNTP's may, but need not be labeled with a label of known molecular weight.

A reagent may be affixed to a substrate. In other aspects of the invention, a sample may be affixed to the substrate and made available to a reagent in solution. A reagent or sample may be covalently bound to the substrate or it may be bound by some non covalent interaction including electrostatic, hydrophobic, hydrogen bonding, Van Der Waals, magnetic, or any other interaction by which a reagent capable of specific binding to a marker such as an oligonucleotide probe may be attached to a substrate while maintaining its ability to recognize the marker to which it has specificity. A substrate may be any solid or semi solid material onto which a probe may be affixed, attached or printed, either singly or in the presence of one or more additional probes or samples as is exemplified in a microarray. Examples of substrate materials include but are not limited to polyvinyl, polysterene, polypropylene, polyester or any other plastic, glass, silicon dioxide or other silanes, hydrogels, gold, platinum, microbeads, micelles and other lipid formations, nitrocellulose, or nylon membranes. The substrate may take any form, including a spherical bead or flat surface. For example, the probe may be bound to a substrate in the case of an array or an in situ PCR reaction. The sample may be bound to a substrate in the case of a Southern Blot.

A reagent may include a label. A label may be any substance capable of aiding a machine, detector, sensor, device, or enhanced or unenhanced human eye from differentiating a labeled composition from an unlabeled composition. Examples of labels include but are not limited to: a radioactive isotope or chelate thereof, dye (fluorescent or nonfluorescent,) stain, enzyme, or nonradioactive metal. Specific examples include but are not limited to: fluorescein, biotin, digoxigenin, alkaline phosphatese, biotin, streptavidin, $^3$H, $^{14}$C, $^{32}$P, $^{35}$S, or any other compound capable of emitting radiation, rhodamine, 4-(4'-dimethylamino-phenylazo)benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that may be differentially detected. The label may also include one or more fluorescent dyes optimized for use in genotyping. Examples of such dyes include but are not limited to: FAM, dR110, 5-FAM, 6FAM, dR6G, JOE, HEX, VIC, TET, dTAMRA, TAMRA, NED, dROX, PET, BHQ+, Gold540, and LIZ.

nucleotide is an individual deoxyribonucleotide or ribonucleotide base. Examples of nucleotides include but are not limited to: adenine, thymine, guanine, cytosine, and uracil, which may be abbreviated as A, T, G, C, or U in representations of oligonucleotide or polynucleotide sequence. Any molecule of two or more nucleotide bases, whether DNA or RNA, may be termed a nucleic acid.

A nucleic acid reagent may be affixed to a solid substrate. Alternatively, the sample may be affixed to a solid substrate and the oligonucleotide placed into a mixture. For example, the nucleic acid reagent may be bound to a substrate in the case of an array or the sample may be bound to a substrate as the case of a Southern Blot, Northern blot or other method that affixes the sample to a substrate. A nucleic acid reagent or sample may be covalently bound to the substrate or it may be bound by some non covalent interaction including electrostatic, hydrophobic, hydrogen bonding, Van Der Waals, magnetic, or any other interaction by which an oligonucleotide may be attached to a substrate while maintaining its ability to recognize the allele to which it has specificity. A substrate may be any solid or semi solid material onto which a probe may be affixed, attached or printed, either singly or in the formation of a microarray. Examples of substrate materials include but are not limited to polyvinyl, polysterene, polypropylene, polyester or any other plastic, glass, silicon dioxide or other silanes, hydrogels, gold, platinum, microbeads, micelles and other lipid formations, nitrocellulose, or nylon membranes. The substrate may take any shape, including a spherical bead or flat surface.

Nucleic acid amplification may be performed using nucleic acids from any source. In general, nucleic acid amplification is a process by which copies of a nucleic acid may be made from a source nucleic acid. In some nucleic amplification methods, the copies are generated exponentially. Examples of nucleic acid amplification include but are not limited to: the polymerase chain reaction (PCR), ligase chain reaction (LCR,) self-sustained sequence replication (3SR), nucleic acid sequence based amplification (NASBA,) strand displacement amplification (SDA,) amplification with Qβ replicase, whole genome amplification with enzymes such as φ29, whole genome PCR, in vitro transcription with Klenow or any other RNA polymerase, or any other method by which copies of a desired sequence are generated.

Polymerase chain reaction (PCR) is a particular method of amplifying DNA, generally involving the mixing of a nucleic sample, two or more primers, a DNA polymerase, which may be a thermostable DNA polymerase such as Taq or Pfu, and deoxyribose nucleoside triphosphates (dNTP's). In general, the reaction mixture is subjected to temperature cycles comprising a denaturation stage, (typically 80-100° C.) an annealing stage with a temperature that may based on the melting temperature (Tm) of the primers and the degeneracy of the primers, and an extension stage (for example 40-75° C.) In real-time PCR analysis, additional reagents, methods, optical detection systems, and devices are used that allow a measurement of the magnitude of fluorescence in proportion to concentration of amplified DNA. In such analyses, incorporation of fluorescent dye into the amplified strands may be detected or labeled probes that bind to a specific sequence during the annealing phase release their fluorescent tags during the extension phase. Either of these will allow a quantification of the amount of specific DNA present in the initial sample. RNA may be detected by PCR analysis by creating a DNA template from RNA through a reverse transcriptase enzyme. In some aspects of the invention, the marker may be detected by quantitative PCR analysis, which may be performed using a kit containing components that facilitate genotyping analysis. Genotyping analysis may be performed using a probe that is capable of hybridizing to a nucleic acid sequence of interest.

An oligonucleotide is a reagent capable of binding a nucleic acid sequence. An oligonucleotide may be any polynucleotide of at least 2 nucleotides. Oligonucleotides may be less than 10, less than 15, less than 20, less than 30, less than 40, less than 50, less than 75, less than 100, less than 200, less than 500, or more than 500 nucleotides in length. While oligonucleotides are often linear, they may, depending on their sequence and conditions, assume a two- or three-dimensional structure. Oligonucleotides may be chemically synthesized by any of a number of methods including sequential synthesis, solid phase synthesis, or any other synthesis method now known or yet to be disclosed. Alternatively, oligonucleotides may be produced by recombinant DNA based methods. One skilled in the art would understand the length of oligonucleotide necessary to perform a particular task. Oligonucleotides may be directly labeled, used as primers in PCR or sequencing reactions, or bound directly to a solid substrate as in oligonucleotide arrays.

Oligonucleotide synthesis is the chemical synthesis of oligonucleotides with a defined chemical structure and/or nucleic acid sequence by any method now known in the art or yet to be disclosed. Oligonucleotide synthesis may be carried out by the addition of nucleotide residues to the 5'-terminus of a growing chain. Elements of oligonucleotide synthesis include: De-blocking (detritylation): A DMT group is removed with a solution of an acid, such as TCA or Dichloroacetic acid (DCA), in an inert solvent (dichloromethane or toluene) and washed out, resulting in a free 5' hydroxyl group on the first base. Coupling: A nucleoside phosphoramidite (or a mixture of several phosphoramidites) is activated by an acidic azole catalyst, tetrazole, 2-ethylthiotetrazole, 2-bezylthiotetrazole, 4,5-dicyanoimidazole, or a number of similar compounds. This mixture is brought in contact with the starting solid support (first coupling) or oligonucleotide precursor (following couplings) whose 5'-hydroxy group reacts with the activated phosphoramidite moiety of the incoming nucleoside phosphoramidite to form a phosphite triester linkage. The phosphoramidite coupling may be carried out in anhydrous acetonitrile. Unbound reagents and by-products may be removed by washing. Capping: A small percentage of the solid support-bound 5'-OH groups (0.1 to 1%) remain unreacted and should be permanently blocked from further chain elongation to prevent the formation of oligonucleotides with an internal base deletion commonly referred to as (n−1) shortmers. This is done by acetylation of the unreacted 5'-hydroxy groups using a mixture of acetic anhydride and 1-methylimidazole as a catalyst. Excess reagents are removed by washing. Oxidation: The newly formed tricoordinated phosphite triester linkage is of limited stability under the conditions of oligonucleotide synthesis. The treatment of the support-bound material with iodine and water in the presence of a weak base (pyridine, lutidine, or collidine) oxidizes the phosphite triester into a tetracoordinated phosphate triester, a protected precursor of the naturally occurring phosphate diester internucleosidic linkage. This step can be substituted with a sulfurization step to obtain oligonucleotide phosphorothioates. In the latter case, the sulfurization step is carried out prior to capping. Upon the completion of the chain assembly, the product may be released from the solid phase to solution, deprotected, and collected. Products may be isolated by HPLC to obtain the desired oligonucleotides in high purity.

Kits that facilitate methods of detecting a marker may include one or more of the following reagents: specific nucleic acids such as oligonucleotides, labeling reagents, enzymes including PCR amplification reagents such as the thermostable DNA polymerases Taq or Pfu, reverse transcriptase, or one or more other polymerases, and/or reagents that facilitate hybridization. Specific nucleic acids may include nucleic acids, polynucleotides, oligonucleotides (DNA, or RNA), or any combination of molecules that includes one or more of the above, or any other molecular entity capable of specific binding to a nucleic acid marker. In one aspect of the invention, the specific nucleic acid comprises one or more oligonucleotides capable of hybridizing to the marker.

A kit may also contain an indication of a result of the use of the kit that signifies a particular characteristic. An indication includes any guide to a result that would signal the presence or absence of any characteristic that the kit is configured to predict. For example, the indication may be expressed numerically, expressed as a color or density of a color, expressed as an intensity of a band, derived from a standard curve, or expressed in comparison to a control. The indication may be communicated through the use of a writing. A writing may be any communication of the result in a tangible medium of expression. The writing may be contained physically in or on the kit (on a piece of paper for example), posted on the Internet, mailed to the user separately from the kit, or embedded in a software package. The writing may be in any medium that communicates how the result may be used to predict the cellular or physiological characteristic that the kit is intended to predict, such as a printed document, a photograph, sound, color, or any combination thereof.

The influenza virus is a member of the family orthomyxoviridae viruses, including Influenzavirus A, Influenzavirus B, and Influenzavirus C. There are multiple serotypes of Influenza A typed according to their hemagglutinin and neuraminidase type including H1N1, H1N2, H2N2, H3N1, H3N2, H3N8, H5N1, H5N2, H5N3, H5N8, H5N9, H7N1, H7N2, H7N3, H7N4, H7N7, H9N2, and H10N7. Further genotypic and phenotypic variances in the Influenza virus may interchangeably be called strains, subtypes, or variants.

An antiviral drug may be any composition of matter that adversely affects viral replication, infectivity, ability to evade the immune system or any other feature of a virus that promotes its ability to replicate or infect a cell. Antiviral drugs used in the treatment of influenza include adamantanes such as amantadine and rimantadine as well as neuraminidase inhibitors such as zanamivir and oseltamivir.

EXAMPLE 1

Elements and acts in the examples are intended to illustrate the invention for the sake of simplicity and have not necessarily been rendered according to any particular sequence or embodiment. The example is also intended to establish possession of the invention by the Inventors.

Real Time PCR (RTPCR) was performed in 10 µl reaction volumes in 384-well Clear Optical Reaction Plates. In each 10 µl reaction, 1 µl of template was added to 9 µl of qPCR reaction mix containing 900 nM of each Forward and Reverse primer (listed in Table 1), 225 nM of the appropriate TaqMan MGB or BHQ probe (listed in Table 1), 1× TaqMan Universal PCR Master Mix (Applied Biosystems), and molecular-grade water. Separate reactions were carried out with either the sensitive or the resistant allele-specific primer. All reactions were performed in triplicate. Amplification and real-time fluorescence detections were performed on a Real Time PCR System using and the following PCR incubations: 3 min at 50° C.; 10 min at 95° C.; and 40 cycles of the following: 15 s at 95° C., and 1 min at 60°. A manual Ct threshold was set at 0.2 and the baseline was automatically selected. A Ct value was obtained for each reaction using sequence detection software.

Primer and Probe Sequences (key)

| Oligo Name | Sequence ID |
|---|---|
| SF-SS F primer | SEQ ID NO. 1 |
| SF-SS R primer | SEQ ID NO. 2 |
| SF-SS probe | SEQ ID NO. 3 |
| S31N F primer | SEQ ID NO. 4 |
| S31N R-Sensitive | SEQ ID NO. 5 |
| S31N R-Resistant | SEQ ID NO. 6 |
| S31N probe | SEQ ID NO. 7 |
| H274Y F primer | SEQ ID NO. 8 |
| H274Y R-Sensitive | SEQ ID NO. 9 |
| H274Y R-Resistant | SEQ ID NO. 10 |
| H274Y Probe | SEQ ID NO. 11 |

Assay performance characteristics were established by comparing clinical study results with the CDC rRT-PCR Swine Flu Panel for detection of 2009 H1N1 Influenza RNA in respiratory swabs (see Example 2)

Sixty-three samples were received. The samples were received as extracted Total Nucleic Acid (TNA) and were extracted using the MagNA Pure LC TNA kit. All of the samples were previously determined to be either positive or negative for 2009 H1N1 by the CDC 2009 H1N1 influenza virus assay panel. Using the CDC panel, 38 of the samples were previously determined to be positive for H1N1/09 and 25 of the samples were previously determined to be negative for H1N1/09. The disclosed test agreed with the CDC panel that 31 of the 38 positive samples were positive. The disclosed test agreed with the CDC panel that 23 of the 25 negative samples were negative.

Genomic DNA or RNA of organisms that are closely related or could cause similar symptoms in a patient as Influenza A were assayed in duplicate across the disclosed H1N1/09 detection assay, and the disclosed assay that detects antiviral drug resistant strains of H1N1/09 by the presence of an H274Y mutation in the neuraminidase gene. No cross reactivity to any respiratory pathogens was seen. RNA from three H1N1/09 samples was run as a positive control to show typical Ct values.

| Pathogen | Source | H1N1/09 Ct value | H274Y Ct value | |
|---|---|---|---|---|
| | | | Resistant | Sensitive |
| Adenovirus-7 | ATCC | >50 | >50 | >50 |
| Adenovirus-7 | ATCC | >50 | >50 | >50 |
| B. parapertussis | ATCC | >50 | >50 | >50 |
| B. parapertussis | ATCC | >50 | >50 | >50 |
| B. pertussis | ATCC | >50 | >50 | >50 |
| B. pertussis | ATCC | >50 | >50 | >50 |
| C. burnetii | TGen | >50 | >50 | >50 |
| C. burnetii | TGen | >50 | >50 | >50 |
| Influenza B | AZDHS | >50 | >50 | >50 |
| Influenza B | AZDHS | >50 | >50 | >50 |
| Influenza B | AZDHS | >50 | >50 | >50 |
| Influenza B | AZDHS | >50 | >50 | >50 |
| Influenza B | AZDHS | >50 | >50 | >50 |

-continued

| Pathogen | Source | H1N1/09 Ct value | H274Y Ct value | |
|---|---|---|---|---|
| | | | Resistant | Sensitive |
| Influenza B | AZDHS | >50 | >50 | >50 |
| L. pneumophila | TGen | >50 | >50 | >50 |
| L. pneumophila | TGen | >50 | >50 | >50 |
| M. pneumoniae | TGen | >50 | >50 | >50 |
| M. pneumoniae | TGen | >50 | >50 | >50 |
| MRSA | TGen | >50 | >50 | >50 |
| MRSA | TGen | >50 | >50 | >50 |
| MSSA | TGen | >50 | >50 | >50 |
| MSSA | TGen | >50 | >50 | >50 |
| Mycobacterium tuberculosis (MTB) | ATCC | >50 | >50 | >50 |
| Mycobacterium tuberculosis (MTB) | ATCC | >50 | >50 | >50 |
| RSV A | ATCC | >50 | >50 | >50 |
| RSV A | ATCC | >50 | >50 | >50 |
| RSV B | ATCC | >50 | >50 | >50 |
| RSV B | ATCC | >50 | >50 | >50 |
| nH1N1 #1 | AZDHS | 21.30 | >50 | 24.34 |
| nH1N1 #2 | AZDHS | 23.76 | >50 | 26.20 |
| nH1N1 #3 | AZDHS | 24.91 | >50 | 27.90 |

Figure 2:
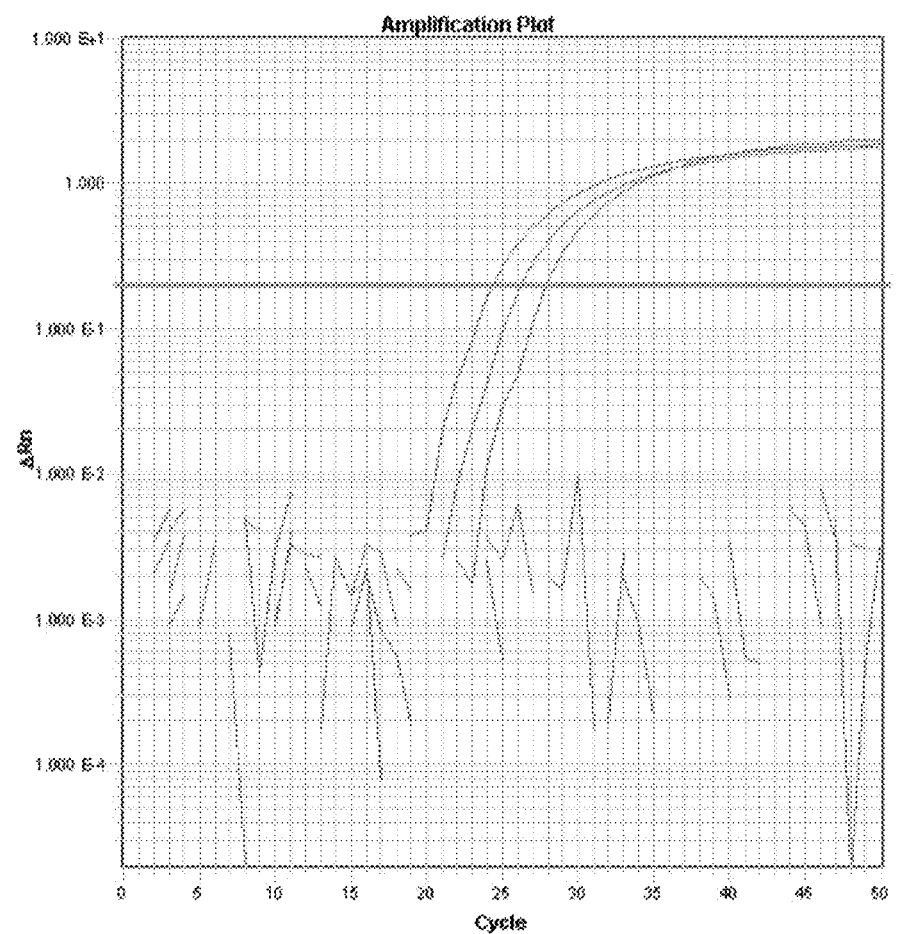
FIG. 2 depicts an amplification plot of three H1N1/09 positive samples shown to lack the H274Y antiviral drug resistance mutation using a primer/probe set that includes SEQ ID NO. 8, SEQ ID NO. 9, and SEQ ID NO. 11.

Referring now to FIG. 1 which depicts an amplification plot that shows a single sample of H1N1/09 previously determined as such by the CDC H1N1/09 rRTPCR panel. The sample was run in triplicate with the disclosed assay to be used in detection of H1N1/09. The green line is the assay threshold. The Ct value (the point at which the amplification plot crosses the threshold) for this particular run was 29. Referring now to FIG. 2 which depicts an amplification plot using three samples that lack the H274Y mutation which confers resistance to antiviral drugs such as Oseltamivir. All three amplified using a primer set that includes SEQ ID NO. 9 as a forward primer. None amplified using a primer set that includes SEQ ID NO. 10 as a forward primer.

Figure 3:
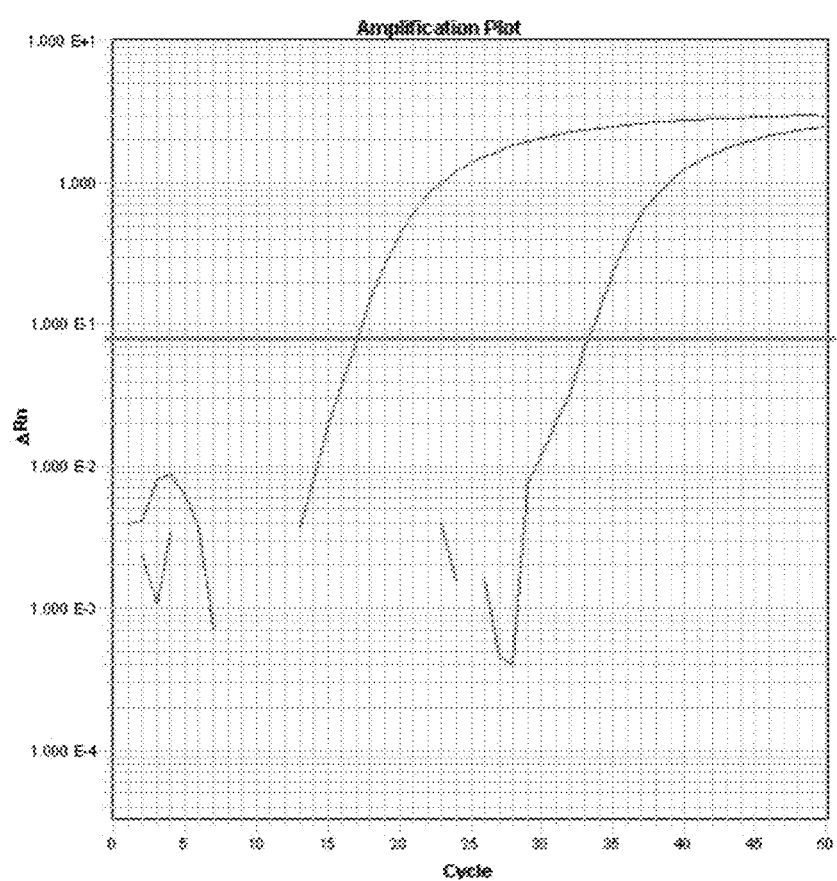
FIG. 3 depicts an amplification plot of a control plasmid that includes the H274Y antiviral drug resistance mutation. The line on the left, indicating a Ct of 17 was generated using a primer/probe set that includes SEQ ID NO. 8, SEQ ID NO. 10, and SEQ ID NO. 11. The line on the right was generated using a primer/probe set that includes SEQ ID NO. 8, SEQ ID NO. 9, and SEQ ID NO. 11.

Referring now to FIG. 3, which depicts an amplification plot that shows detection of a plasmid standard that includes the H274Y mutation. The standard amplified with a Ct value of about 17 using a primer set that included SEQ ID NO. 10 as a forward primer and amplified with a Ct value of about 38 using a primer set that included SEQ ID NO. 9 as a forward primer.

REFERENCES

The publications referenced in the following numbered paragraphs are hereby incorporated by reference in their entirety. They are included to reduce the length and complexity of the detailed description. Inventors expressly reserve the right to prove a date of invention prior to the publication date of any of the references listed below.

1. CDC Realtime rRTPCR Protocol for Detection and Characterization of Swine Influenza A (H1N1), CDC REF. #I-007-05, Version 2009: Swine Influenza, published 29 Apr. 2009.
2. U.S. patent application Ser. No. 12/908,536, filed 20 Oct. 2010.
3. Li B et al, *Genomics* 83, 311-320 (2004).
4. Germer S et al, *Genome Res* 10, 258-266 (2000).
5. Sidwell R W et al, *Antiviral Res* 68, 10-17 (2005).
6. McSharry J J et al, *Clin Diag Lab Immunol* 11, 21-28 (2004).
7. Sidwell R W and Smee D F, *Antiviral Res* 48, 1-16 (2000).
8. Mungall B A et al, *Avian Dis* 47, 3Suppl 1141-1144 (2003).
9. Gubareva L V et al, *J Gen Virol* 83, 2683-2692 (2002).
10. Hata M et al, *Jpn J Infect Dis* 60, 202-204 (2007).

11. Suwannakarn K et al, *J Virol Methods* 152, 25-31 (2008).
12. Carr M J et al, *J Virol Methods* 153, 257-262 (2008).
13. Duwe S and Schweiger B *J Virol Methods* 153, 134-141 (2008).
14. Deyde V M et al *Antiviral Res* 81, 16-24 (2008.)
15. Rahman M et al, *Diagn Microbiol Infect Dis* 62, 162-166 (2007).
16. Lu Y Y et al, *Lett Appl Microbiol* 46, 20-25 (2007).
17. Rowley C F et al, *J Virol Methods* 149, 69-75 (2008).
18. Peuchant O et al, *AIDS* 31, 1417-1423 (2008).
19. Schwarz G et al, *Nucleic Acids Res* 11, e24 (2004).
20. Norton N et al, *Hum Genet* 110, 471-478 (2002).
21. Archambeault et al, *Blood* 111, 1124-1127 (2007).
22. Ottone T et al, *J Mol Diagn* 10, 212-216 (2008).
23. Hirt C et al, *Br. J. Haematol* 141, 631-640 (2008).

We claim:

1. A method of determining whether or not H1N1/09 is present in a sample comprising:

adding a first oligonucleotide that includes a sequence selected from the group consisting of SEQ ID NO. 1, SEQ ID NO. 2, and SEQ ID NO. 3 to a first mixture comprising the sample;

subjecting the first mixture to conditions that allow nucleic acid amplification;

adding an oligonucleotide that includes a sequence selected from the group consisting of SEQ ID NO. 9 and SEQ ID NO. 10 to a second mixture comprising the sample;

adding a second oligonucleotide that includes SEQ ID NO. 8 to the second mixture comprising the sample;

subjecting the second mixture to conditions that allow nucleic acid amplification; and classifying the sample into a cohort on the basis of a result of the nucleic acid amplification of the first mixture and a result of the nucleic acid amplification of the second mixture, wherein the cohort is selected from the group consisting of: a cohort of samples in which H1N1/09 is present and is sensitive to an antiviral composition; a cohort of samples in which H1N1/09 is present and is resistant to an antiviral composition; and a cohort of samples in which H1N1/09 is absent.

2. The method of claim 1 wherein the first oligonucleotide includes SEQ ID NO. 1 further comprising adding a second oligonucleotide to the first mixture.

3. The method of claim 2 wherein the second oligonucleotide in the first mixture includes SEQ ID NO. 2.

4. The method of claim 2 further comprising adding a third oligonucleotide to the first mixture.

5. The method of claim 4 wherein the third oligonucleotide includes SEQ ID NO. 3.

6. The method of claim 4 wherein the third oligonucleotide comprises a label.

7. The method of claim 6 wherein the third oligonucleotide comprises a fluorescent label.

8. The method of claim 7 wherein the third oligonucleotide comprises a fluorescent label selected from the group consisting of FAM, dR110, 5-FAM, 6FAM, dR6G, JOE, HEX, VIC, TET, dTAMRA, TAMRA, NED, dROX, PET, BHQ+, Gold540, and LIZ.

9. The method of claim 1 wherein the result comprises a Ct value.

10. The method of claim 1 wherein the result comprises a nucleic acid sequence.

11. The method of claim 1 wherein the sample comprises an environmental sample.

12. The method of claim 1 wherein the sample is derived from a subject.

13. The method of claim 12 wherein the sample comprises a sputum sample.

14. The method of claim 12 wherein the sample comprises a respiratory swab.

15. The method of claim 1 further comprising adding a third oligonucleotide to the second mixture, wherein the third oligonucleotide includes SEQ ID NO. 11.

16. The method of claim 1 wherein the antiviral composition comprises a neuraminidase inhibitor.

17. The method of claim 1 wherein amplification in the first mixture indicates the presence of H1N1/09 in the sample.

18. The method of claim 1 wherein amplification in the second mixture with the oligonucleotide including SEQ ID NO. 10 indicates resistance to the antiviral composition.

19. The method of claim 1 wherein amplification with the oligonucleotide including SEQ ID NO. 9 and no amplification with the oligonucleotide including SEQ ID NO. 10 indicate sensitivity to the antiviral composition.

* * * * *